United States Patent
Frigg

(10) Patent No.: US 10,675,068 B2
(45) Date of Patent: Jun. 9, 2020

(54) FIXATION DEVICE FOR TREATING A BONE FRACTURE

(75) Inventor: Robert Frigg, Langendorf (CH)

(73) Assignee: DePuy Synthes Products, Inc., Raynham, MA (US)

( * ) Notice: Subject to any disclaimer, the term of this patent is extended or adjusted under 35 U.S.C. 154(b) by 908 days.

(21) Appl. No.: 13/278,805

(22) Filed: Oct. 21, 2011

(65) Prior Publication Data

US 2012/0109128 A1  May 3, 2012

Related U.S. Application Data

(60) Provisional application No. 61/407,231, filed on Oct. 27, 2010.

(51) Int. Cl.
*A61B 17/68* (2006.01)
*A61B 17/74* (2006.01)

(52) U.S. Cl.
CPC .......... *A61B 17/746* (2013.01); *A61B 17/744* (2013.01); *A61B 17/748* (2013.01)

(58) Field of Classification Search
USPC ............................................ 606/62–68, 320
See application file for complete search history.

(56) References Cited

U.S. PATENT DOCUMENTS

| | | | | |
|---|---|---|---|---|
| 2,381,050 A | * | 8/1945 | Hardinge | 606/65 |
| 3,554,193 A | * | 1/1971 | Konstantinou et al. | 606/65 |
| RE32,488 E | * | 9/1987 | Gustilo et al. | 623/23.35 |
| 4,791,918 A | * | 12/1988 | Von Hasselbach | 606/65 |
| 5,084,050 A | * | 1/1992 | Draenert | A61F 2/30767 |
| | | | | 606/304 |
| 5,376,125 A | * | 12/1994 | Winkler | 623/23.11 |
| 5,658,339 A | * | 8/1997 | Tronzo et al. | 606/67 |
| 5,984,926 A | * | 11/1999 | Jones | A61B 17/686 |
| | | | | 606/309 |
| 5,993,486 A | * | 11/1999 | Tomatsu | 623/13.11 |
| 6,139,552 A | * | 10/2000 | Horiuchi | 606/88 |
| 6,238,126 B1 | | 5/2001 | Dall | |
| 6,296,644 B1 | * | 10/2001 | Saurat | A61B 17/7013 |
| | | | | 606/256 |
| 6,375,684 B1 | * | 4/2002 | Kriek | 623/23.39 |

(Continued)

FOREIGN PATENT DOCUMENTS

| AU | 4360289 | 2/1990 |
|---|---|---|
| CN | 2852972 | 1/2007 |

(Continued)

OTHER PUBLICATIONS http://www.thefreedictionary.com/ball-and-socket+joint, accessed May 5, 2015.*

*Primary Examiner* — Jan Christopher L Merene
(74) *Attorney, Agent, or Firm* — Fay Kaplun & Marcin, LLP

(57) ABSTRACT

A fixation device for treating an epiphyseal fracture, comprises a shaft extending longitudinally along a central axis from a first end to a second end configured to slidably engage a bone implant opening and a having a maximum radius r and a spherical head element attached to the first end of the shaft and having a radius R>r, the spherical head element configured to be inserted into a fragmented portion of bone such that the fragmented portion rotates about the spherical head element relative to the central axis of the shaft.

10 Claims, 13 Drawing Sheets

(56) References Cited

U.S. PATENT DOCUMENTS

| | | | |
|---|---|---|---|
| 6,663,632 B1 | 12/2003 | Frigg | |
| 7,828,828 B2* | 11/2010 | Lim et al. | 606/300 |
| 7,951,198 B2* | 5/2011 | Sucec | A61B 17/562 |
| | | | 606/300 |
| 8,137,350 B2* | 3/2012 | Nakamura | 606/65 |
| 8,317,845 B2* | 11/2012 | Stinnette | 606/306 |
| 8,617,227 B2* | 12/2013 | Sucec et al. | 606/328 |
| 8,926,611 B2* | 1/2015 | Keller et al. | 606/62 |
| 8,956,394 B1* | 2/2015 | McDonnell | A61B 17/686 |
| | | | 606/300 |
| 2002/0107520 A1 | 8/2002 | Hoffman | |
| 2003/0069582 A1* | 4/2003 | Culbert | 606/65 |
| 2005/0113927 A1* | 5/2005 | Malek | A61B 17/7008 |
| | | | 623/17.16 |
| 2006/0074421 A1* | 4/2006 | Bickley | A61B 17/686 |
| | | | 606/290 |
| 2006/0217720 A1* | 9/2006 | Chieng | 606/65 |
| 2006/0229609 A1* | 10/2006 | Wang | A61B 17/7023 |
| | | | 606/257 |
| 2006/0235414 A1* | 10/2006 | Lim et al. | 606/73 |
| 2006/0271054 A1* | 11/2006 | Sucec | A61B 17/562 |
| | | | 606/310 |
| 2008/0077142 A1* | 3/2008 | James et al. | 606/69 |
| 2010/0023011 A1* | 1/2010 | Nakamura | 606/64 |
| 2010/0211112 A1 | 8/2010 | Kuster et al. | |
| 2010/0217265 A1 | 8/2010 | Chen et al. | |
| 2011/0066152 A1* | 3/2011 | Keller et al. | 606/62 |
| 2011/0106177 A1* | 5/2011 | Lewis | A61B 17/686 |
| | | | 606/305 |
| 2012/0259372 A1* | 10/2012 | Glazer | A61B 17/686 |
| | | | 606/301 |
| 2014/0094803 A1* | 4/2014 | Overes et al. | 606/66 |

FOREIGN PATENT DOCUMENTS

| | | |
|---|---|---|
| JP | H0898846 | 4/1996 |
| TW | 201031381 | 9/2010 |
| WO | 92/12691 | 8/1992 |
| WO | 98/01078 | 1/1998 |
| WO | 98/34567 | 8/1998 |
| WO | 2005/094707 | 10/2005 |

* cited by examiner

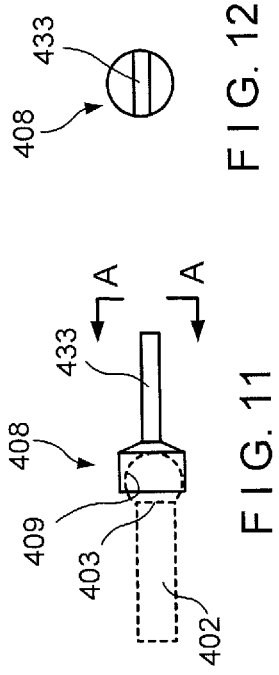
FIG. 12
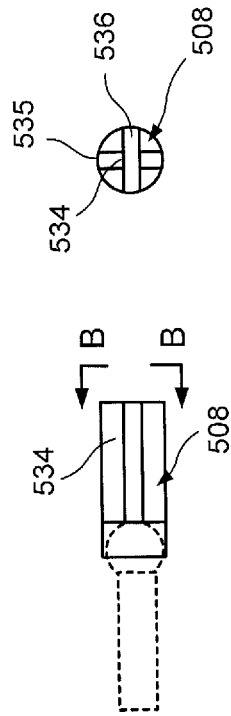
FIG. 14
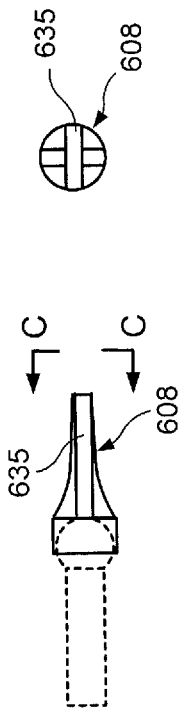
FIG. 16
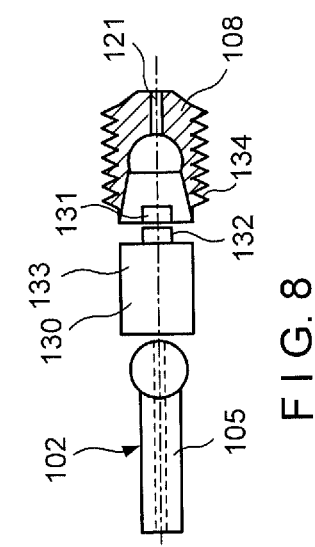
FIG. 11
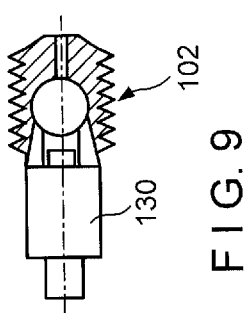
FIG. 13
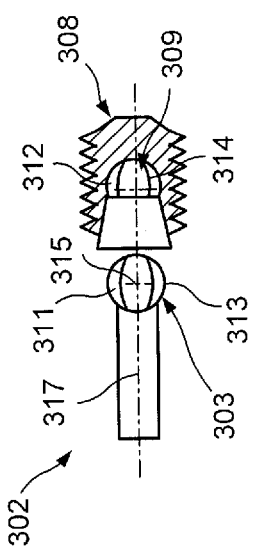
FIG. 15
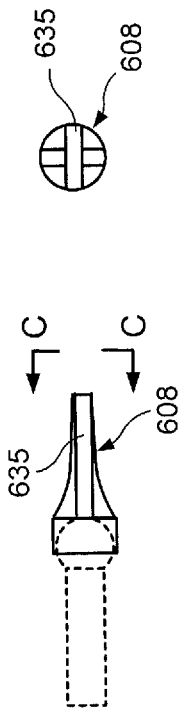
FIG. 8
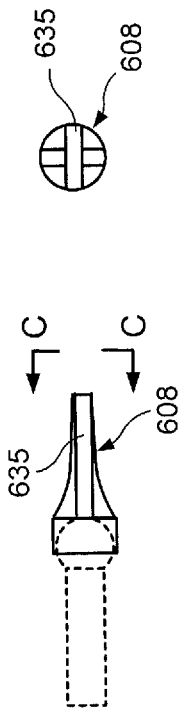
FIG. 9
FIG. 10

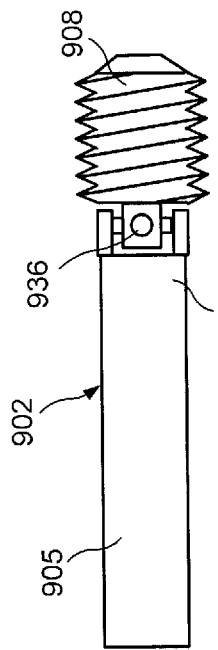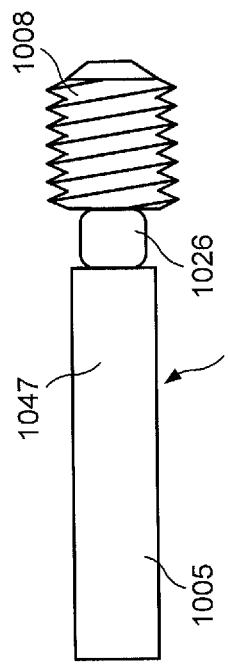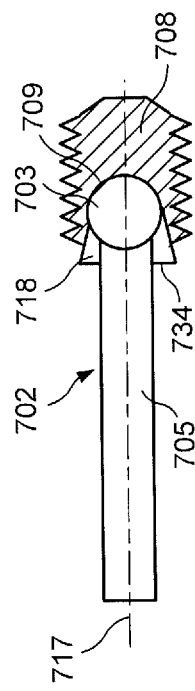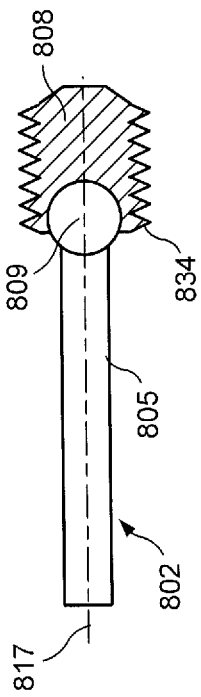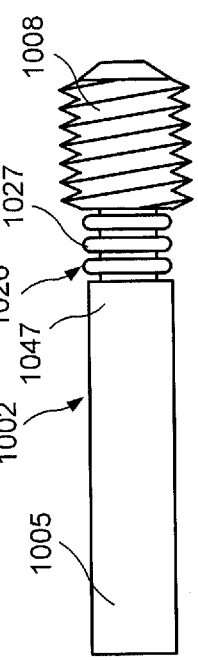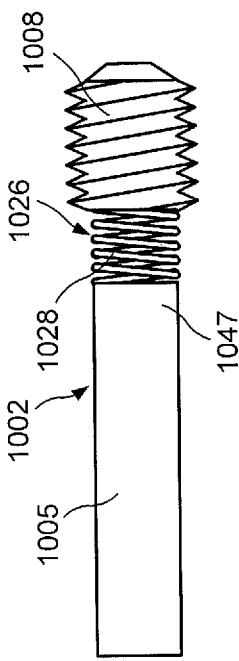
FIG. 17
FIG. 18
FIG. 19
FIG. 20
FIG. 21
FIG. 22

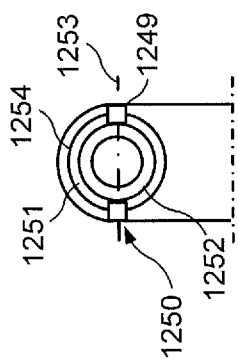
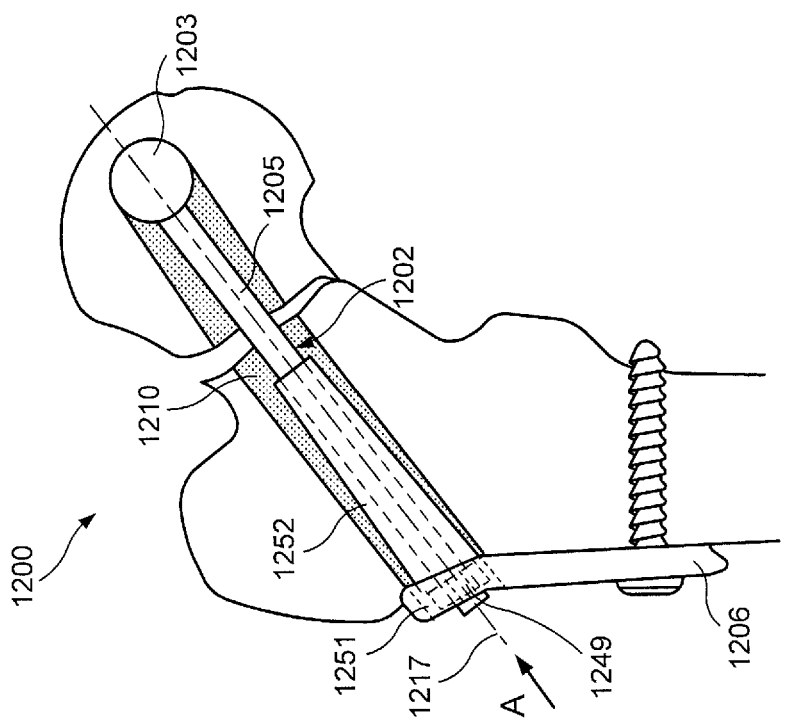

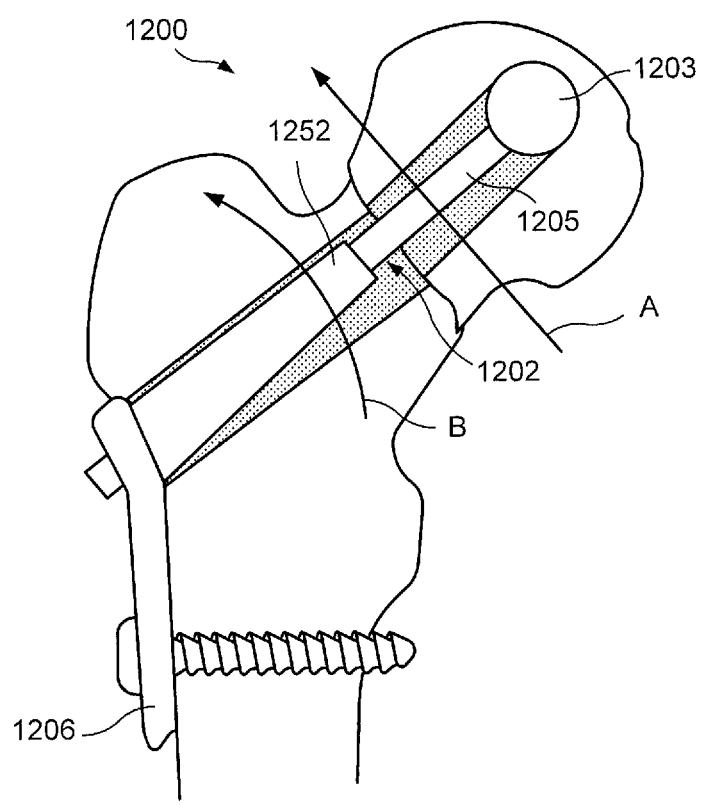
F I G. 30

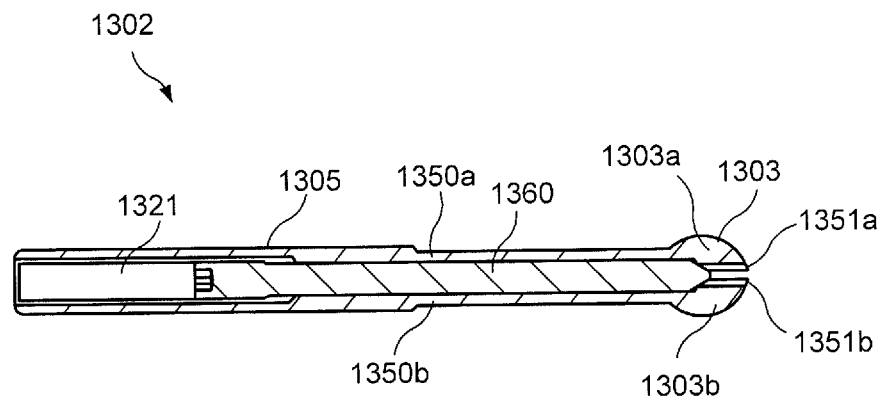
F I G. 33
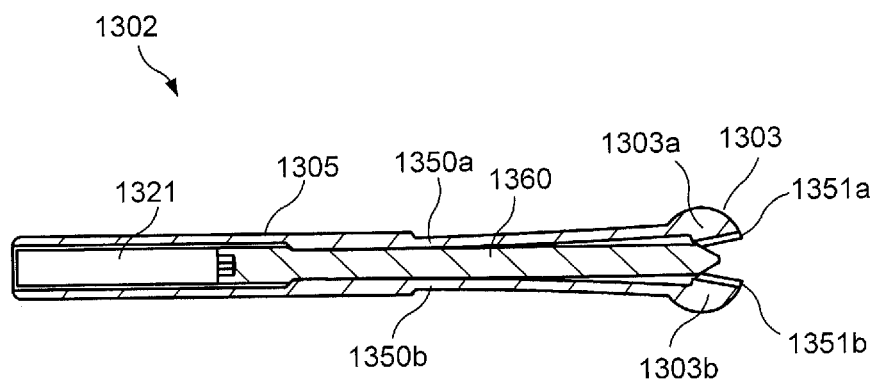
F I G. 34

FIXATION DEVICE FOR TREATING A BONE FRACTURE

PRIORITY CLAIM

The present application claims priority to U.S. Provisional Application Ser. No. 61/407,231 entitled "Bone Implant" and filed on Oct. 27, 2010 to Robert Frigg. The entire contents of this application are incorporated herein by reference.

FIELD OF THE INVENTION

The present invention generally relates to a device for treating fractures. In particular, the present invention relates to a device comprising a fixation element that may be used with a bone plate or intramedullary nail to treat a fracture in the epiphyseal portion of the bone.

BACKGROUND

A fracture in the epiphyseal portion of a long bone may be treated with a femoral implant such as a femoral neck screw. These femoral neck screws may be coupled to a bone plate or an intramedullary nail such that the neck screws are axially displaceable relative to the bone plate or intramedullary nail to allow a dynamization in the direction of the axis of the femoral neck screw and provide an angular stability between the femoral neck screw and the bone plate or intramedullary nail.

In some cases where the fracture has not been properly reduced, however, implantation of the femoral neck screw may result in only a limited contact area between the fractured portions of the bone. Dynamization via the femoral neck screw often does not compensate for inadequate or improper fracture reduction resulting from, for example, misalignment of the two fragments. Insufficient fracture contact area can delay fracture healing which in turn can lead to cyclic overload of the screw anchorage in the femoral head. This cyclic overload may lead to implant loosening and/or implant cut out. Insufficient fracture reduction often occurs in the sagittal plane, as visualization of the fracture site in this plane is very difficult during surgical interventions. Rotation of the head fragment may increase the risk of implant cut out due to incorrect positioning of the screw.

SUMMARY OF THE INVENTION

The present invention relates to a bone implant comprising an epiphyseal fixation element including a shaft extending along a central axis from a first end to a second end and having a maximum radius r and a spherical head element attached to the first end of the shaft, the spherical head element having a radius $R>r$. The bone implant further comprises a bone plate or an intramedullary nail to which the second end of the shaft is slidably engageable. This bone implant may be used for both the proximal and distal femur, the proximal tibia and the humerus.

Some advantages of the bone implant according to the present invention are that the spherical head element of the fixation element permit the epiphyseal fragment, e.g. the femoral head, to pivot about the center of the spherical head element, thus allowing a partial compensation of an inadequate fracture reduction and the pivotable fixation of the epiphyseal fragment, e.g. the femoral head, at the implant along with the slidable configuration between the longitudinal shaft and the bone plate or intramedullary nail allows the epiphyseal fragment to pivot and axially displace until the fracture gap is closed. Thus, the fracture stability is improved due to a distribution of the physical load over a larger bone contact area between the two fragments.

In one exemplary embodiment of the bone implant, the ratio r/R is at least 0.65, and preferably at least 0.7.

In a further exemplary embodiment of the bone implant, the ratio r/R is at most 0.9, and preferably at most 0.8. For a femoral neck fracture, such a ratio permits, under normal conditions, the femoral head to pivot about the center of the spherical head element in an angular range from between $-15°$ and $-20°$ to between $+15°$ and $+20°$ relative to the central axis.

In a further exemplary embodiment of the bone implant, the shaft is cylindrical.

In yet a further exemplary embodiment of the bone implant, the shaft is connected to the bone plate or intramedullary nail via a joint with one or more plastically deformable connecting elements to pivotably connect the sleeve to the bone plate or intramedullary nail, preferably via a cardan joint. This configuration has an advantage that the shaft can tilt so that the epiphyseal fragment can be displaced in a direction transverse to the central axis of the epiphyseal fixation element.

In another exemplary embodiment of the bone implant, the longitudinal shaft and the spherical head element are cannulated.

According to a further aspect of the present invention, a bone implant comprises an epiphyseal fixation element including a longitudinal shaft extending along a central axis from a first end to a second end and having a maximum radius r and a bone anchoring element movably coupled to the first end of the shaft and which has an outer diameter that is larger than a diameter of the longitudinal shaft. The implant further comprises a bone plate or an intramedullary nail to which the second end the shaft is slidably engageable.

Some advantages of the bone implant according to the exemplary embodiments of the present invention are that the articulated coupling between the bone anchoring element and the longitudinal shaft of the fixation element permits the epiphyseal fragment, e.g. the femoral head, to pivot thus allowing for at least a partial compensation of inadequate fracture reduction and the pivotable fixation of the epiphyseal fragment, e.g. the femoral head, and the anchoring element together with the axially slidable configuration of the longitudinal shaft of the implant allows the epiphyseal fragment to pivot and/or axially displace until the fracture gap is closed. Thus, fracture stability is improved due to distribution of the physical load over a larger bone contact area between the two fragments.

In an exemplary embodiment of the bone implant, the bone anchoring element is coupled to the first end of the shaft via a ball-and-socket joint.

In a further exemplary embodiment of the bone implant, the bone anchoring element is linked to the first end of the shaft via a cardan joint.

In a further exemplary embodiment of the bone implant, the bone anchoring element is coupled to the first end of the shaft via a compliant member.

In yet a further exemplary embodiment of the bone implant, the compliant member is a metallic or plastic bellow.

In another exemplary embodiment of the bone implant, the compliant member is a metallic or plastic spring.

In another exemplary embodiment of the bone implant, the compliant member comprises an elastomer.

In yet another exemplary embodiment of the bone implant, the shaft is connected to the bone plate or intramedullary nail by means of a joint with one or more plastically deformable connecting elements to pivotably connect the sleeve to the bone plate or intramedullary nail, preferably via a cardan joint. Thus, this embodiment has the advantage that the shaft is able to tilt in so that the epiphyseal fragment can be displaced in a direction transverse to the central axis of the epiphyseal fixation element.

In yet another exemplary embodiment of the bone implant, the shaft is cylindrical. In this case the maximum radius r coincides with the radius of the circular cross-sectional area.

In still another exemplary embodiment of the bone implant, the longitudinal shaft and the bone anchoring element are cannulated.

In a further exemplary embodiment of the bone implant, the fixation element comprises a spherical head element fixed or fixable to an end of the shaft. The spherical head element has a radius R>r and wherein the bone anchoring element comprises a spherical cavity having the radius R for receiving the spherical head element in a rotative manner.

In yet a further exemplary embodiment of the bone implant, the spherical head element is cannulated.

In another exemplary embodiment of the bone implant, the ratio r/R is at least 0.65, and preferably at least 0.7.

In another exemplary embodiment of the bone implant, the ratio r/R is at most 0.9, and preferably at most 0.8. For a femoral neck fracture, such a ratio permits, under normal conditions, the femoral head to pivot about the center of the spherical head element in an angular range from between −15° and −20° to between +15° and 20° relative to the central axis.

In a further exemplary embodiment of the bone implant, the bone anchoring element has a tapered opening located between an outer surface of the bone anchoring element and the spherical cavity, wherein the diameter of the tapered opening decreases towards the spherical cavity. The tapered opening permits a greater angulation between the longitudinal shaft and the bone anchoring element.

In yet a further exemplary embodiment of the bone implant, the spherical cavity tapers toward an outer surface of the bone anchoring element such that the spherical head element may be snapped into the spherical cavity.

In another exemplary embodiment of the bone implant, the spherical head element and the spherical cavity each have flattened surface portions corresponding to one another. The corresponding flattened surfaces prevent the bone anchoring element from rotating about the central axis of the epiphyseal fixation element while still permitting the bone anchoring element to pivot about the center of the spherical head element in a variety of planes which contain the central axis of the epiphyseal fixation element.

In yet another exemplary embodiment of the bone implant, the spherical head element and the cavity each comprise a plurality of circular edges located between the flattened surface portions.

In yet another exemplary embodiment of the bone implant, the circular edges have one common center coinciding with the center of the spherical head element.

In yet another exemplary embodiment of the bone implant, the spherical head element and the spherical cavity each have a polygonal cross-sectional area orthogonal to the central axis of the epiphyseal fixation element, preferably a hexagonal cross-sectional area.

In a further exemplary embodiment of the bone implant, the bone anchoring element includes an external thread.

In yet a further exemplary embodiment of the bone implant, the bone anchoring element includes one of a blade, a cross blade and a helical blade for fixation in the bone.

In still a further exemplary embodiment of the bone implant, the bone anchoring element is not coaxially arranged with respect to the central axis of the longitudinal shaft.

According to a further exemplary embodiment of the present invention, a bone implant comprises an epiphyseal fixation element including a longitudinal shaft extending along a central axis from a proximal portion to a distal portion and having a maximum radius r and a bone anchoring element which is movably coupled to the distal portion of the shaft and which has a diameter larger than a diameter of the longitudinal shaft. The bone implant further comprises a sleeve comprising a central bore to slidably receive the proximal portion of the longitudinal shaft, wherein the proximal portion of the shaft and the sleeve comprise one or more transverse bores for receiving a bone screw.

Some of the advantages of the bone implant according to the exemplary embodiment of the present invention are that the articulated coupling of the bone anchoring element to the longitudinal shaft of the fixation element permits the epiphyseal fragment, e.g. the humeral head, to pivot thus allowing the bone implant to partially compensate for an inadequate fracture reduction. In addition, the pivotable fixation of the epiphyseal fragment, e.g. the humeral head, at the implant together with the axial slidable configuration of the anchoring element relative to the longitudinal shaft of the implant allow the epiphyseal fragment to pivot and axially displace until the fracture gap is closed. Thus, the fracture stability is improved due to a distribution of the physical load over a larger bone contact area between the two fragments.

In an exemplary embodiment of the bone implant, the bone anchoring element is coupled to the first end of the shaft via a ball-and-socket joint.

In a further exemplary embodiment of the bone implant, the bone anchoring element is coupled to the first end of the shaft via a cardan joint.

In another exemplary embodiment of the bone implant, the bone anchoring element is coupled to the first end of the shaft via a compliant member.

In another exemplary embodiment of the bone implant, the compliant member is a metallic or plastic bellow.

In a further exemplary embodiment of the bone implant, the compliant member is a metallic or plastic spring.

In yet a further exemplary embodiment of the bone implant, the compliant member comprises an elastomer.

In still a further exemplary embodiment of the bone implant, the shaft is cylindrical. In this embodiment, the maximum radius r coincides with the radius of the circular cross-sectional area.

In another exemplary embodiment of the bone implant, the longitudinal shaft and the bone anchoring element are cannulated.

In yet another exemplary embodiment of the bone implant, the fixation element comprises a spherical head which is slidably arranged on the front portion of the longitudinal shaft and wherein the bone anchoring element comprises a spherical cavity having the radius R for receiving the spherical head element in a rotative manner.

In yet another exemplary embodiment, the bone implant comprises an inner sleeve for receiving the shaft and a joint with one or more plastically deformable connecting elements to pivotably connect the inner sleeve to the sleeve, preferably via a cardan joint. Thus, the shaft is configured to tilt such that the epiphyseal fragment can be displaced in a direction transverse to the central axis of the epiphyseal fixation element.

In a further exemplary embodiment of the bone implant, the spherical head element is cannulated.

In a further exemplary embodiment of the bone implant, the ratio r/R is at least 0.65, and preferably at least 0.7.

In a further exemplary embodiment of the bone implant, the ratio r/R is at most 0.9, and preferably at most 0.8. For a subcapital humeral fracture, such a ratio permits, under normal conditions, the humeral head fragment to pivot about the center of the spherical head element in an angular range from between −15° and −20° to between +15° and 20° relative to the central axis.

In another exemplary embodiment of the bone implant, the bone anchoring element includes a tapered opening located between an outer surface of the bone anchoring element and the spherical cavity, wherein the diameter of the tapered opening decreases towards the spherical cavity to permit a greater angulation between the longitudinal shaft and the bone anchoring element.

In another exemplary embodiment of the bone implant, the spherical cavity tapers towards an outer surface of the bone anchoring element in such that the spherical head element may be snapped into the spherical cavity.

In yet another exemplary embodiment of the bone implant, the spherical head element and the spherical cavity each include flattened surface portions corresponding to one another, the corresponding flattened surfaces prevent the bone anchoring element from rotating about the central axis of the epiphyseal fixation element while still permitting the bone anchoring element to pivot about the center of the spherical head element in a variety of planes which contain the central axis of the epiphyseal fixation element.

In yet another exemplary embodiment of the bone implant, the spherical head element and the cavity each comprise a plurality of circular edges located between the flattened surface portions.

In a further exemplary embodiment of the bone implant, the circular edges have one common center coinciding with the center of the spherical head element and the center of the spherical cavity.

In a further exemplary embodiment of the bone implant, the spherical head element and the spherical cavity each have a polygonal cross-sectional area orthogonal to the central axis of the epiphyseal fixation element, preferably a hexagonal cross-sectional area.

In yet a further exemplary embodiment of the bone implant, the bone anchoring element includes an external thread.

In still a further exemplary embodiment of the bone implant, the bone anchoring element includes one of a blade, a cross blade and a helical blade for fixation in the bone.

In yet a further exemplary embodiment of the bone implant, the bone anchoring element is not coaxially arranged with respect to the central axis of the longitudinal shaft.

According to a further exemplary embodiment of the present invention, a method for treating an epiphyseal bone fracture using the bone implant comprises the following steps:
  a) positioning a guide wire in the long bone obliquely relative to the axis of the long bone and penetrating through a shaft fragment of the long bone and into an epiphyseal fragment;
  b) drilling a bore hole into the long bone from a lateral surface of the long bone to accommodate the spherical head element or the bone anchoring element so that, when inserted, the spherical head element or the bone anchoring element provides a center of rotation for the epiphyseal bone fragment in a desired position. The bore hole may be drilled using a guide wire as a guidance for a drill bit; and
  c) inserting the epiphyseal fixation element into the bore hole as far as the spherical head segment or the bone anchoring element offers the desired center of rotation of the epiphyseal bone fragment.

The direction and the depth of the bore hole may be determined using one or more X-ray images so that the spherical head element or the anchoring element can be inserted such that the center of rotation of the epiphyseal bone fragment is positioned at a desired location within the bone fragment.

In one embodiment of the method, the method further comprises the step of inserting an intramedullary nail into the medullar cavity of a long bone to be treated before performing the step a).

In a further exemplary embodiment, the method comprises after step c) the steps of positioning a bone plate by sliding the barrel over the longitudinal shaft until the bone plate abuts a lateral surface of the long bone and fastening the bone plate to the long bone using one or more bone screws.

In yet a further embodiment, the method comprises after step c) the steps of positioning a sleeve within the bore hole by sliding the sleeve over the longitudinal shaft until the sleeve is completely inserted into the long bone and fastening the sleeve and the rear portion of the longitudinal shaft to the long using one or more bone screws.

In another exemplary embodiment, the method comprises after step c) the step of repositioning the fracture by using a lever coupled to a sleeve which receives the epiphyseal fixation element and which in turn is coupled to a bone plate or an intramedullary nail via a joint including plastically deformable pivot pins between the sleeve and the bone plate or the intramedullary nail.

BRIEF DESCRIPTION OF THE DRAWINGS

Several embodiments of the invention will be described in the following by way of example and with reference to the accompanying drawings in which:

FIG. 8 illustrates an exploded view of the fixation element of the embodiment of FIG. 3 and an insertion tool;

FIG. 9 illustrates a longitudinal section through the fixation element of the embodiment of FIG. 3 together with an insertion tool;

FIG. 10 illustrates a longitudinal section through a fixation element of a further embodiment of the bone implant according to the invention;

FIG. 11 illustrates a lateral view of an anchoring element of another embodiment of the bone implant according to the invention;

FIG. 12 illustrates a front view of the anchoring element of FIG. 11 viewed in the direction A indicated in FIG. 11;

FIG. 13 illustrates a lateral view of an anchoring element of a further embodiment of the bone implant according to the invention;

FIG. 14 illustrates a front view of the anchoring element of FIG. 13 viewed in the direction B indicated in FIG. 13;

FIG. 15 illustrates a lateral view of an anchoring element of again a further embodiment of the bone implant according to the invention;

FIG. 16 illustrates a front view of the anchoring element of FIG. 15 viewed in the direction C indicated in FIG. 15;

FIG. 17 illustrates a longitudinal section through the fixation element of the embodiment of the bone implant according to FIG. 3;

FIG. 18 illustrates a longitudinal section through a fixation element of another embodiment of the bone implant according to the invention;

FIG. 19 illustrates a lateral view of a fixation element of again another embodiment of the bone implant according to the invention;

FIG. 20 illustrates a lateral view of a fixation element of yet another embodiment of the bone implant according to the invention;

FIG. 21 illustrates a lateral view of a fixation element of still another embodiment of the bone implant according to the invention;

FIG. 22 illustrates a lateral view of a fixation element of a further embodiment of the bone implant according to the invention;

FIGS. 25a and 25b illustrate the maximal axial dynamization in a longitudinal section through a front portion of a fixation element of the embodiment of the bone implant according to FIG. 23;

FIG. 27 illustrates a lateral view of another embodiment of the bone implant according to the invention;

FIG. 28 illustrates a front view of the embodiment of the bone implant according to FIG. 27 viewed in the direction indicated by arrow A in FIG. 27;

FIG. 30 illustrates a lateral view of the embodiment of the bone implant of FIG. 27 with the rotated femoral head fragment displaced in a proximal direction;

FIG. 33 illustrates a sectional view of a part of the bone implant shown in FIG. 31 in the first non-expanded configuration; and FIG. 34 illustrates a sectional view of a part of the bone implant shown in FIG. 31 in the second expanded configuration.

DETAILED DESCRIPTION

Figure 1:
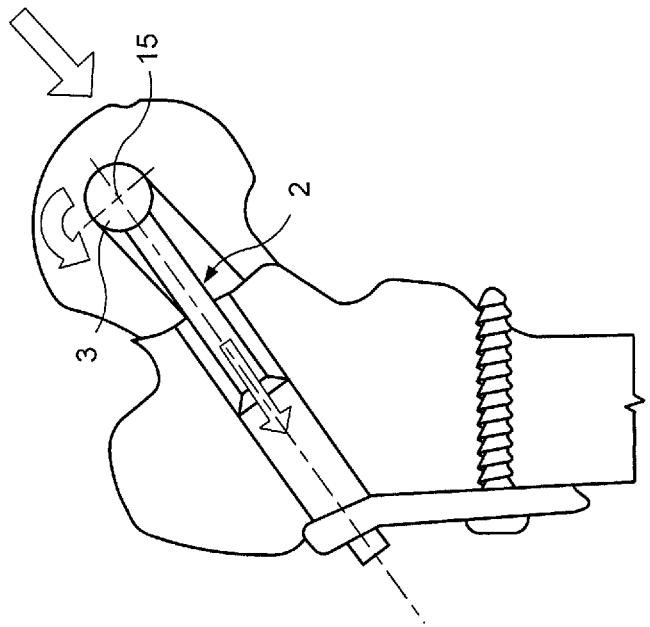
FIG. 1 illustrates a lateral view of an embodiment of the bone implant according to the invention.

The present invention may be further understood with reference to the following description and the appended drawings, wherein like elements are referred to with the same reference numerals. The present invention relates to a device for treating fractures and, in particular, relates to a device for treating a fracture in an epiphyseal portion of a long bone such as a femur. Exemplary embodiments of the present invention describe a fixation element that may be used with an implant such as a bone plate or an intramedullary nail to be inserted via a lateral surface of the bone through the fracture and into a head portion thereof. The fixation element comprises a longitudinal shaft including a spherical portion at an end thereof, which is positioned within the head portion of the bone such that the head portion is pivotable about the spherical portion to facilitate proper reduction of the fracture. It should be note that the terms proximal and distal, as used herein, are intended to refer to a direction toward (proximal) and away from (distal) a user of the device.

Figure 2:
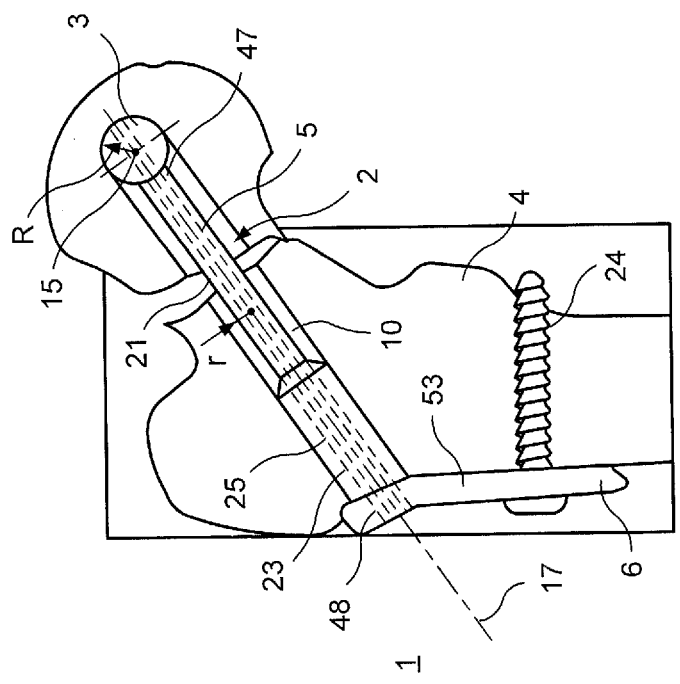
FIG. 2 illustrates a lateral view of the embodiment of the bone implant of FIG. 1 with the femoral head fragment rotated about the spherical head element.

As shown in FIGS. 1 and 2, an implant 1 according to an exemplary embodiment of the present invention comprises a fixation element 2 configured as a hip screw for treating a femoral neck fracture and a bone plate 6. The fixation element 2 includes a shaft 5 extending longitudinally along a central axis 17 from a first distal end 47 to a second proximal end 48 and a spherical head element 3 at the first end 47. The spherical head element 3 has a center 15 and a diameter D that is larger than a diameter d of the shaft 5. The spherical head element 3 may be integrally formed with the shaft 5 or coupleable to the first end 47 of the shaft 5. The diameter d of the shaft 5 may be about 75% of the diameter D of the spherical head element 3. Further, the fixation element 2 may also include a cannulation 21 extending through the fixation element 2 coaxially with the central axis 17.

The bone plate 6 includes a longitudinal body portion 53 and a barrel 23 extending transversely from the body portion 53. The body portion 53 according to this embodiment sized and shaped to be attached to a long bone 4 (e.g., the femur) and includes an opening sized and shaped to receive therethrough a bone fixation screw 24 for fixing the bone plate 6 to the bone. The barrel 23 includes a through hole 25 sized and shaped to slidably accommodate the shaft 5 of the fixation element 2 such that the spherical head element 3 extends distally past a distal end of the barrel 23. The slidable arrangement between the shaft 5 and the barrel 23 of the bone plate 6 permits the fixation element 2 to be moved relative to the bone plate 6 along the central axis 17 of the fixation element 2, facilitating dynamization of the fracture in the direction of the central axis 17 of the fixation element 2. The fixation element 2 extending through the barrel 23 also provides angular stability between the fixation element 2 and the bone plate 6.

In use, the barrel 23 is positioned over the shaft 5 after the spherical head element 3 has been located correctly in a bone fragment. The shaft 5 is slidable within the barrel 23 and is able to move, for example, post-operatively. In this way, a reduction of the bone fragment is achieved under the natural influence of the muscles, gravity, etc., trying to return to the bone to its original pre-fracture configuration. The fixation element 2 remains in position post-operatively due to the same natural influences. However, as would be understood by the skilled person additional features can be used to resist unexpected or unwanted movement of the fixation element 2. For example, the internal diameter of the barrel 23 can be sized to provide friction forces that resist movement other than the movement due to the natural influences. In another example, an o-ring type device can be used to resist the unwanted movement. Other ways are of course possible, as the skilled person would understand.

A bore hole 10 is drilled into the proximal femur from a lateral surface of the femur substantially coaxial with or parallel to the axis of the femoral neck. The bore hole 10 has a diameter corresponding to the diameter D of the spherical head element 3 so that the spherical head element 3 fits through the bore hole 10 to be positioned in the femoral head. The fixation element 2 is advanced through the bore hole 10 in the proximal femur until the spherical head element 3 reaches an end of the bore hole 10 and the femoral head fragment is seated on the spherical head element 3. Since the diameter of the bore hole 10 in the proximal femur is larger than the diameter d of the shaft 5, the femoral head fragment is polyaxially rotatable about the center 15 of the spherical head element 3 within a predetermined range of angulation.

In some cases where the femoral neck fracture is improperly and/or inadequately reduced prior to the placement of the fixation element 2, the two bone fragments will have only a limited contact area relative to each other, as shown in FIG. 1. The dynamization alone, i.e. a coaxial movement of the fixation element 2 towards the bone plate 6, cannot compensate for inadequate fracture reduction. It will be understood by those of skill in the art that an insufficient fracture contact area may lead to delayed fracture healing which in turn may lead to cyclic overload of the anchorage of the fixation element 2 in the femoral head. A cyclic overload may result in implant loosening and/or implant cutout. An insufficient fracture reduction often occurs in the sagittal plane as the visualization in this plane is very difficult during surgical intervention.

Figures 3, 4:
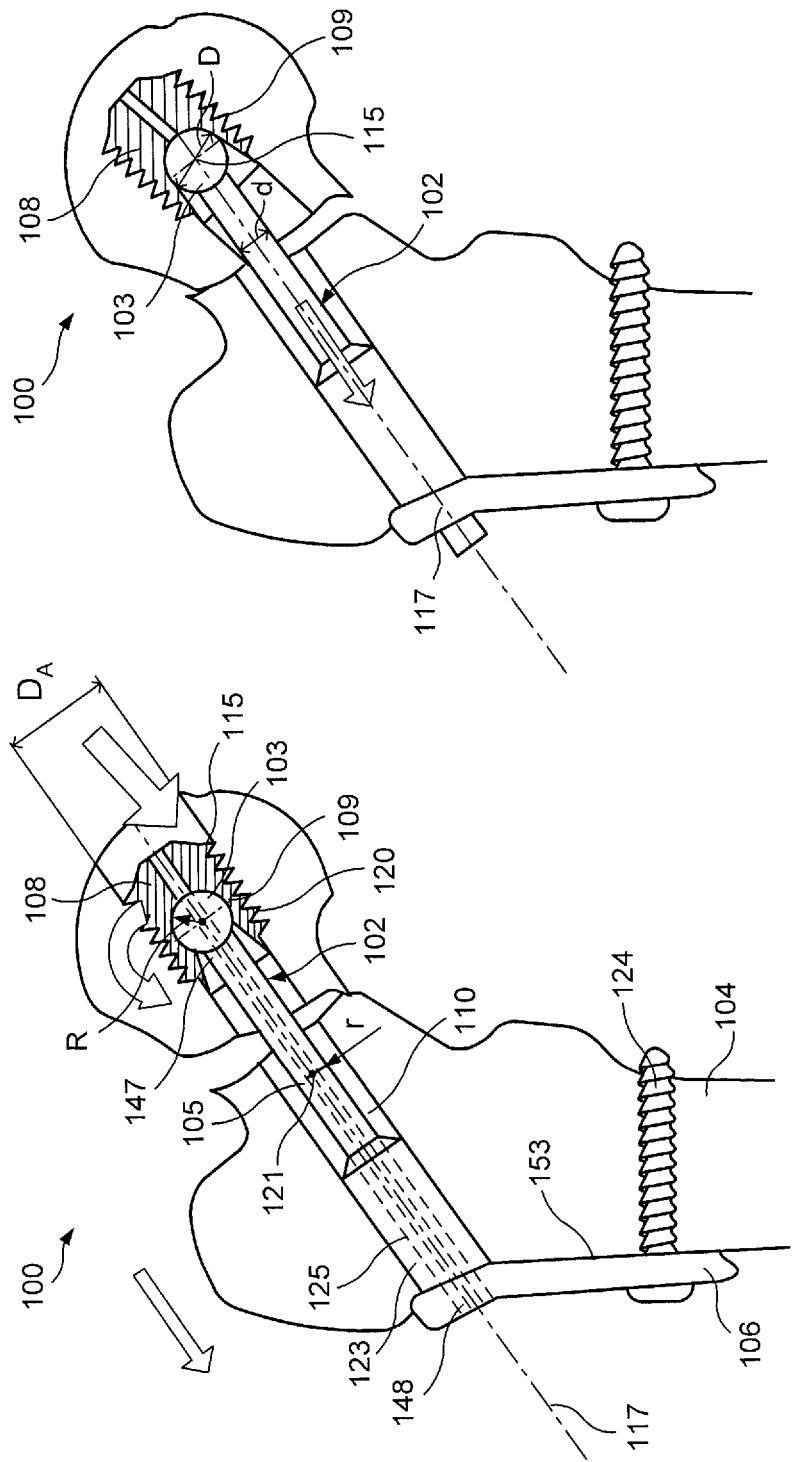
FIG. 3 illustrates a lateral view of another embodiment of the bone implant according to the invention.
FIG. 4 illustrates a lateral view of the embodiment of the bone implant of FIG. 3 with the femoral head pivoted and the fracture gap closed.

Rotation of the femoral head fragment about the center 15 of the spherical head element 3 at least partially compensates for inadequate fracture reduction. Thus, as illustrated in FIG. 3, fracture stability is improved via both the axial dynamization and rotation of the femoral head fragment since the physiological load is spread over a larger contact area of the bone fragments.

As shown in FIGS. 3 to 6, a bone implant 100 according to another exemplary embodiment of the present invention is substantially similar to the bone implant 1, as described above. The bone implant 100 comprises a fixation element 102 configured as a hip screw for treating a femoral neck fracture and a bone plate 106. The bone plate 106 is substantially similar to the bone plate 6, comprising a longitudinal body portion 153 and a barrel 123 extending transversely therefrom. The fixation element 102 is also substantially similar to the fixation element 2, but further comprises an anchoring element 108 coupled to a first end 147 of a longitudinal shaft 105 thereof such that the fixation element 102 may be anchored in the femoral head portion of the bone.

The fixation element 102 includes a shaft 105 extending longitudinally along a central axis 117 from a first end 147 to a second end 148 and a spherical head element 103 at the first end 147. The spherical head element 103 has a center 115 and a diameter D larger than a diameter d of the shaft 105. The diameter d may be approximately 75% of the diameter D of the spherical head element 103.

The fixation element 102 further comprises the anchoring element 108 coupled to the spherical head element 103. The anchoring element 108 includes a spherical cavity 109 sized and shaped to receive the spherical head element 103 so that a ball-and-socket joint is formed between the anchoring element 108 and the shaft 105. The anchoring element 108 has an external thread 120 with a diameter $D_A$ configured to be screwed into the femoral head fragment. Further, the fixation element 102 includes a cannulation 121 extending through said the shaft 105, the spherical head element 103 and the anchoring element 108 of the fixation element 102 coaxial or parallel to the central axis 117.

Similarly to the embodiment of FIGS. 1 and 2, a bore hole 110 is drilled into the proximal femur from the lateral surface of the femur to extend coaxially with or parallel to the axis of the femoral neck. The bore hole 110 has a diameter corresponding to the core diameter of the external thread 120 of the anchoring element 8 so that the external thread 120 can cut into the bone tissue of the femoral head fragment. Thus, the femoral head fragment is fixed to the anchoring element 108 once the anchoring element 108 has been completely advanced into the bone.

The fixation element 102 is advanced into the bore hole 110 in the proximal femur until the anchoring element 108 is positioned at an end of the bore hole 110 with the femoral head fragment seated on the spherical head element 103 via the anchoring element 108. Because the diameter of the bore hole 110 in the proximal femur is larger than the diameter d of the shaft 5, the femoral head fragment is polyaxially rotatable about the center 15 of the spherical head element 103 within a predetermined range of angulation.

Figure 6:
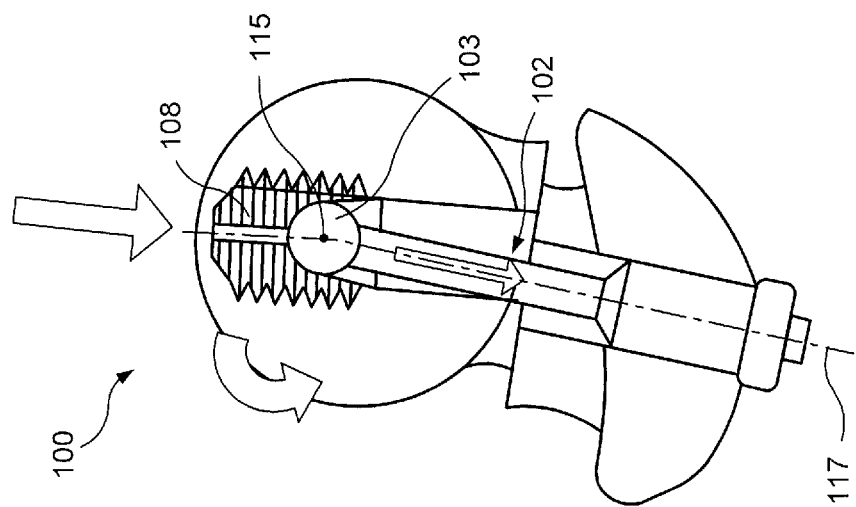
FIG. 6 illustrates a top view of the embodiment of the bone implant of FIG. 3 with the femoral head pivoted and the fracture gap closed.
Figure 5:
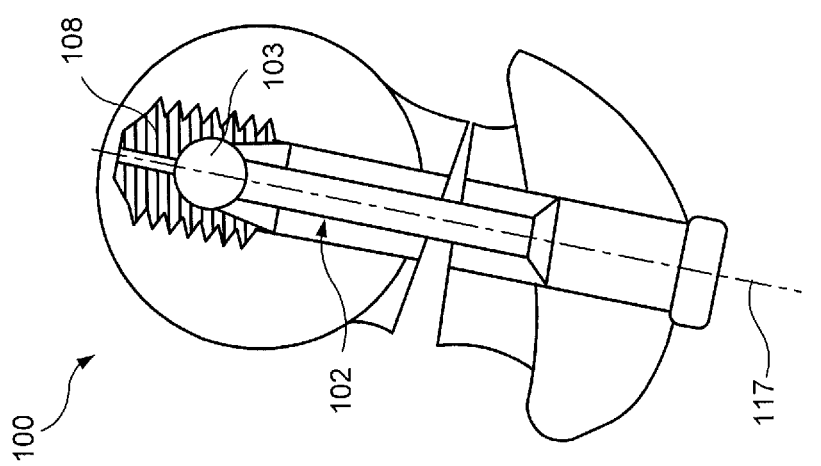
FIG. 5 illustrates a top view of the embodiment of the bone implant of FIG. 3.

Similarly to the bone implant 1 described above, the shaft 105 of the fixation element 102 is slidably received through a through hole 125 of a barrel portion 123 of the bone plate 106. The slidable arrangement of the longitudinal shaft 105 in the through hole 125 facilitates dynamization of the fracture in the direction of the central axis 117 of the fixation element 102 as well as an angular stability between the fixation element 102 and the bone plate 106. Similarly to FIG. 1, FIGS. 3 and 5 illustrate an improper and/or inadequate reduction of a femoral neck fracture prior to the placement of the fixation element 102 such that the two bone fragments have only a limited contact area relative to with one another. The dynamization alone, i.e. coaxial movement of the fixation element 102 towards the bone plate 106, will not fully compensate for the inadequate fracture reduction. As shown in FIGS. 4 and 6, however, the fixation element 102 permits rotation of the anchoring element 108 and, consequently, of the femoral head fragment in which the anchoring element 108 is implanted, about the center 115 of the spherical head element 103, at least partially compensating for the inadequate fracture reduction. The axial dynamization along with the rotation of the femoral head fragment together are able to compensate for the inadequate reduction by spreading the physiological load over a larger contact area of the bone fragments.

Figure 7:
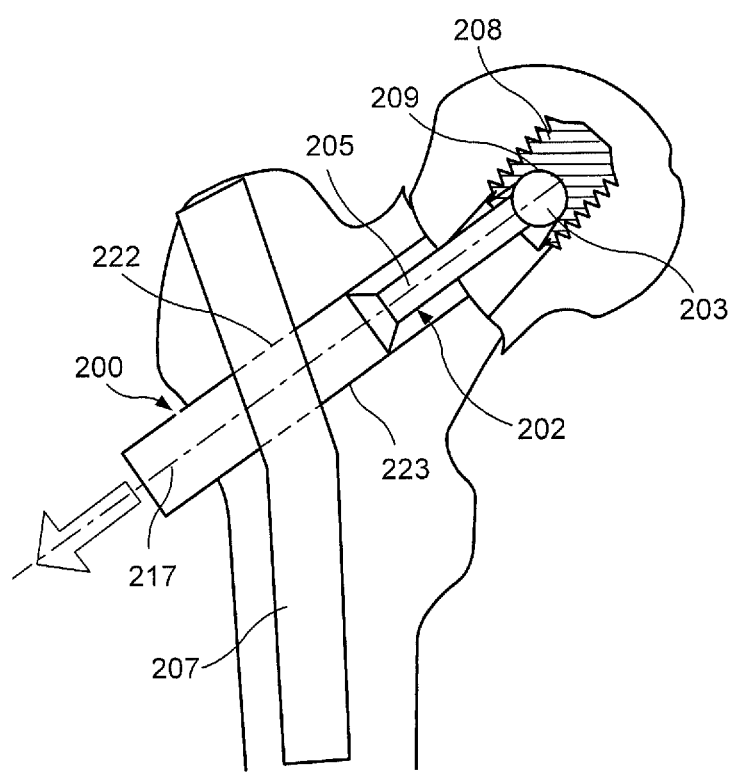
FIG. 7 illustrates a lateral view of again another embodiment of the bone implant according to the invention.

FIG. 7 illustrates a bone implant 200 that is substantially similar to the bone implant 100, as described above, but comprises a fixation element 202 inserted through a portion of an intramedullary nail 207 instead of a bone plate. The fixation element 202 is substantially similar to the fixation element 102 and is configured as a hip screw comprising a longitudinal shaft 205 including a spherical head element 203 at an end thereof and an anchoring element 208 that can be screwed into the femoral head and that has a spherical cavity 209 for receiving the spherical head element 203. As those of skill in the art will understand, the shaft 205 may be slidable within a barrel 223. However, in this embodiment, the shaft 205 is integrally formed with the barrel 223. In this way, the fixation element 202 has the shaft portion 205 and the barrel portion 223, the shaft portion 205 being of a smaller diameter than the barrel portion 223. The fixation element 202 is slidably arranged in a through bore 222 extending through the intramedullary nail 207 transversely relative to a longitudinal axis of the intramedullary nail 207. The slidable arrangement of the fixation element 202 in the through bore 222 in the intramedullary nail 207 permits the fixation element 202 to be moved axially relative to a central axis of the through hole 222 to facilitate dynamization of the fracture in the direction of the central axis 217 of the fixation element 202 while enhancing an angular stability between the fixation element 202 and the intramedullary nail 207. Similarly to the bone fixation element 102, the anchoring element 208 and, consequently, the femoral head fragment in which the anchoring element 208 is implanted, is permitted to rotate about the spherical head element 203 to compensate for inadequate fracture reduction.

FIGS. 8 and 9 illustrate a hollow insertion tool 130 for inserting the anchoring element 108 into the femoral head fragment. It will be understood by those of skill in the art, however, that the hollow insertion tool 130 may be used for the insertion of any of the anchoring elements described herein. The hollow insertion tool 130 includes protrusions 132 at a distal end 133 thereof for engaging a diametrically extending groove 131 with a substantially rectangular cross section at a proximal end 134 of the anchoring element 108 so that the hollow tube 130 may be used to apply a driving (e.g., rotational) force to the anchoring element 108. A shown by FIGS. 8 and 9, the groove 131 is located in a wall of the bone anchoring element 108. In use, after the fixation element 102 including the shaft 105 and anchoring element 108 are inserted, the insertion tool 130 is slid over the shaft 105 to rotate the anchoring element 108. That is, the protrusions 132 are engaged with the grooves 131 and the insertion tool 130 is rotated to screw the anchoring element 108 into the bone fragment. Since the fixation element 102 includes a cannulation 121 extending through the bone anchoring element 108 and the longitudinal shaft 105, the bone anchoring element 108 may be slid along a guiding element, e.g. a Kirschner-wire, when the bone anchoring element 108 is advanced into the bone using the hollow insertion tool 130. As would be understood by the skilled person, the insertion tool 130 can be any suitable size to allow rotation thereof, for example, the shaft of the insertion tool 130 that extends along the longitudinal shaft 105 can be sized so that it extends externally of the bone implant and can be directly manipulated by the operator or surgeon.

As shown in FIG. 10, a fixation element 302 according to a further embodiment of the present invention is substantially similar to the anchoring element 102 of the bone implant 100, but differs from the fixation element 102 only in that a head element 303 and a cavity 309 in the bone anchoring element 308 each have flattened surface portions 311, 312, respectively, which correspond to one another so that the head element 303 and the cavity 309 are only partially spherical. The flattened surface portions 311, 312 are limited in a cross section orthogonal to a central axis 317 of the fixation element 302 by circular edges 313, 314, respectively, with each circular edge 313, 314 located between two of the flattened surface portions 311, 312. A center formed via the circular edges 314 of the cavity 309 coincides with a center 315 of the head element 303 formed by the circular edges 313. When the spherical head element 303 is inserted in the spherical cavity 309 in the bone anchoring element 308 the bone anchoring element 308 is rotatable in a variety of planes containing the central axis 317 with each plane being defined by one pair of engaged circular edges 313, 314. Thus, the head element 303 and the 309 each have a hexagonal cross-sectional area orthogonal to the central axis 317 of the fixation element 302.

As shown in FIGS. 11 and 12, an anchoring element 408 according to an alternate embodiment is substantially similar to the anchoring element 108 of the bone implant 100 and includes a cavity 409 for accommodating a head element 403 of the bone fixation element 402. However, rather than an external thread, the anchoring element 408 includes a blade 433 extending distally therefrom to engage a femoral head bone fragment when implanted therein.

As shown in FIGS. 13 and 14, an anchoring element 508 according to a further embodiment is substantially similar to the anchoring element 408. The anchoring element 508, however, comprises a cross blade 534. The cross blade 534 includes first and second blade portions 535, 536, respectively, arranged substantially perpendicularly relative to one another when implanted therein.

As shown in FIGS. 15 and 16, an anchoring element 608 according to a further embodiment is substantially similar to the anchoring element 408. However, the anchoring element 608 includes a helical blade 635 extending distally therefrom to engage the formal head bone fragment when implanted therein.

FIG. 17 illustrates a fixation element 702 according to another exemplary embodiment that is substantially similar to the fixation element 102 of the bone implant 100. The fixation element 702, however, comprises an anchoring element 708 including an opening 718 extending from the proximal end 734 of the anchoring element 708 to the spherical cavity 709. A diameter of the opening 718 decreases towards the spherical cavity 709 so that the opening 718 is largest at the proximal end 734 to allow a greater range of angulation between a shaft 705 of and the anchoring element 708. The spherical cavity 709 tapers toward the proximal end 734 so that the spherical head element 703 may be snapped into and/or retained therein.

FIG. 18 illustrates a fixation element 802 according to another embodiment that is substantially similar to the fixation element 102, but which differs therefrom only in that a spherical cavity 809 in the bone anchoring element 808 is open to and arranged closer to a proximal end 834 of the bone anchoring element 808. The cavity 809 extends over an angle which is only little over 180° so that a spherical head element 803 is retained therein while also permitting the bone anchoring element 808 to rotate within a suitable angular range with respect to the central axis 817 without the proximal end 834 of the anchoring element 808 interfering with the shaft 805.

FIG. 19 illustrates a fixation element 902 according to another embodiment that is substantially similar to the fixation element 102, described above. The fixation element 902, however, does not include a spherical head element and a corresponding spherical cavity. Rather, the fixation element 902 comprises an anchoring element 908 coupled to a first end 947 of a longitudinal shaft 905 via a cardan joint 936.

FIGS. 20 to 22 illustrate a fixation element 1002 according to another embodiment substantially similar to the fixation element 902. Rather than a cardan joint, however, the bone anchoring element 1008 is coupled to a first end 1047 of a shaft 1005 via a compliant member 1026. The compliant member 1026 may comprise an elastomer, as illustrated in FIG. 20, or be configured as a bellows 1027, as illustrated in FIG. 21, or as a spring, preferably a helical spring 1028, as illustrated in FIG. 22.

Figure 23:
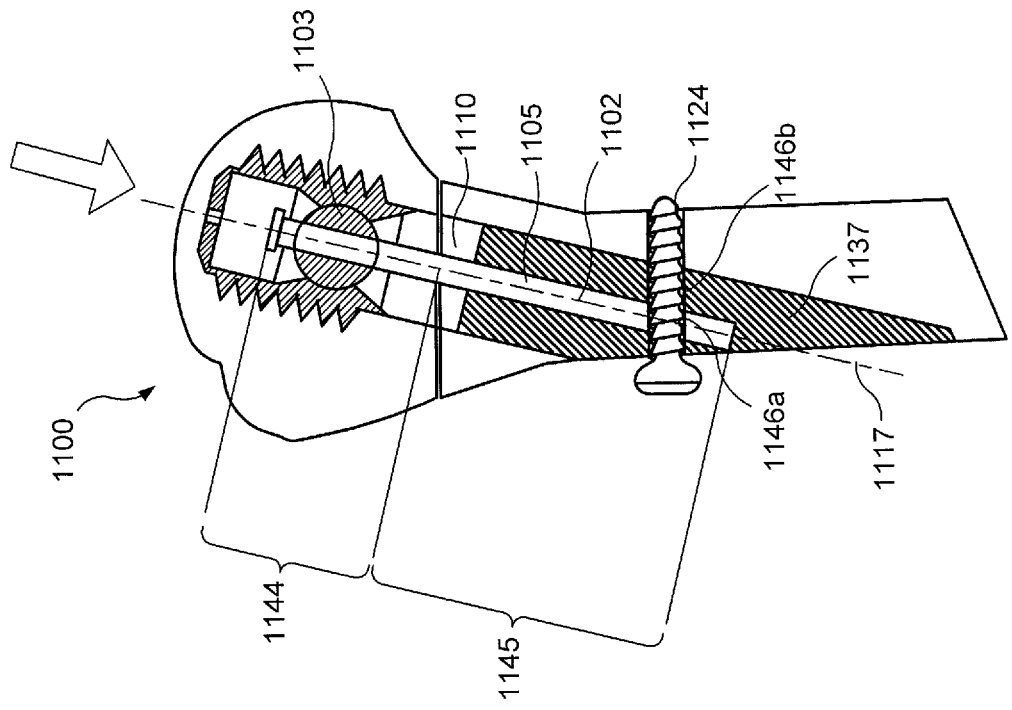
FIG. 23 illustrates a longitudinal section through a further embodiment of the bone implant in case of a treatment of a subcapital humeral head fracture.
Figure 24:
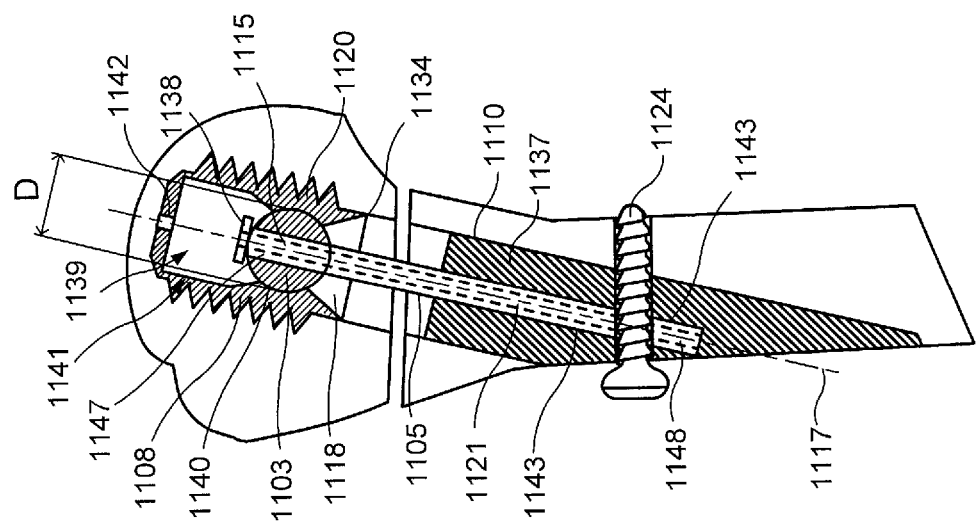
FIG. 24 illustrates a longitudinal section through the embodiment of the bone implant of FIG. 23 with the fracture gap after dynamization.

As shown in FIGS. 23 and 24, a bone implant 1100 according to a further embodiment of the present invention may be used for treating of a subcapital humeral head fracture. The bone implant 1100 comprises a fixation element 1102 and a sleeve 1137.

The fixation element 1102 comprises a shaft 1105, a spherical head element 1103 and an anchoring element 1108. The shaft 1105 extending longitudinally along a central axis 1117 from a first distal end 1147 to a second proximal end 1148. The first end 1147 includes a head 1138 having an enlarged diameter. The spherical head element 1103 may be slidably arranged on a distal portion 1144 of the shaft 1105, proximally of the distal head 1138 of the shaft 1105, such that the shaft 1105 extends through a center 1115 of the spherical head element 1103. A diameter d of the shaft 1105 may be approximately 50% of a diameter D of the spherical head element 1103. A proximal portion 1145 of the shaft 1105 includes a hole 1146a extending transversely therethrough, the hole 1146a configured to receive a shaft portion of a bone screw 1124 therethrough.

The anchoring element 1108 includes a cavity 1139 extending distally from the proximal end 1134 thereof. The cavity 1139 includes an opening 1118 tapering toward a distal end of the anchoring element 1108 and open to a partially spherical section 1140 having the diameter D for receiving the spherical head element 1103 in a polyaxially rotative manner. A diameter of the opening 1118 decreases towards the spherical section 1140 so that the opening is largest at the proximal end 1134 to permit a greater range of angulation is permitted between the longitudinal shaft 1105 of the fixation element 1102 and the anchoring element 1108. The spherical section 1140 includes curved surfaces having a diameter at proximal and distal ends thereof that is smaller than a diameter of a midsection thereof so that the spherical head element 1103 is retained in the spherical section 1140 of the anchoring element 1108. The cavity 1139 further comprises a cylindrical section 1141 extending distally from the spherical section 1140 toward a distal end 1142 of the cavity 1139 for accommodating the head 1138 of the shaft 1105. The anchoring element 1108 is slidable between an extended state where the head 1138 of the shaft 1105 abuts against the spherical head element 1103 and a shortened state where the head 1138 of the shaft 1105 abuts against the distal end 1142 of the cavity 1139. The anchoring element 1108 may have an external thread 1120 configured to be screwed into the femoral head fragment. Further, the fixation element 1102 may comprise a cannulation 1121 extending through the shaft 1105 and the anchoring element 1108 substantially coaxially to the central axis 1117.

Alternatively, as similarly described in the embodiments above, the bone anchoring element 1108 can be slidably and articulately coupled to the longitudinal shaft 1105 via a cardan joint or the bone anchoring element 1108 may be slidably and flexibly linked to the longitudinal shaft 1105 via a compliant member such as, for example, a metallic or plastic bellow, a metallic or plastic spring or an elastomeric element.

The sleeve 1137 extends longitudinally along the central axis 1117 from a proximal end 1149 to a distal end 1150 and includes a central bore 1143 sized and shaped to receive a proximal portion 1145 of the shaft 1105 therein. The sleeve 1137 includes a hole 1146b extending transversely through a portion thereof such that when the sleeve 1137 is slide over the proximal portion 1145 of the shaft 1105, the hole 1146b aligns with the hole 1146a in the shaft 1105 to permit the screw 1124 to be inserted through both holes 1146a, 1146b to fix the bone implant 1100 in the bone.

A bore hole 1110 may be drilled into the proximal humerus from the lateral surface of the humerus extending obliquely relative to a longitudinal axis of the humerus. The bore hole 1110 has a diameter substantially corresponding to a core diameter of the external thread 1120 of the anchoring element 1108 so that the external thread 1120 cuts into the bone tissue of the humeral head fragment as the anchoring element 1108 is driven therein so that the humeral head fragment is fixed to the anchoring element 1108 once the bone anchoring element 1108 has been completely advanced into the bone.

The anchoring element 1108 is advanced into the bore hole 1110 in the proximal humerus until the anchoring element 1108 is positioned at a distal end of the bore hole 1110 and the humeral head fragment is seated on the spherical head element 1103 via the anchoring element 1108. Because the diameter of the bore hole 1110 in the proximal humerus is larger than the diameter d of the shaft 1105 and the cavity 1139 in the anchoring element 1108 has an opening 1118 that is larger at the proximal end 1134 of the anchoring element 1108, the spherical section 40 permits the humeral head fragment to polyaxially rotate about the center 1115 of the spherical head segment 1103 within a predetermined range of angulation.

Figures 25, 26:
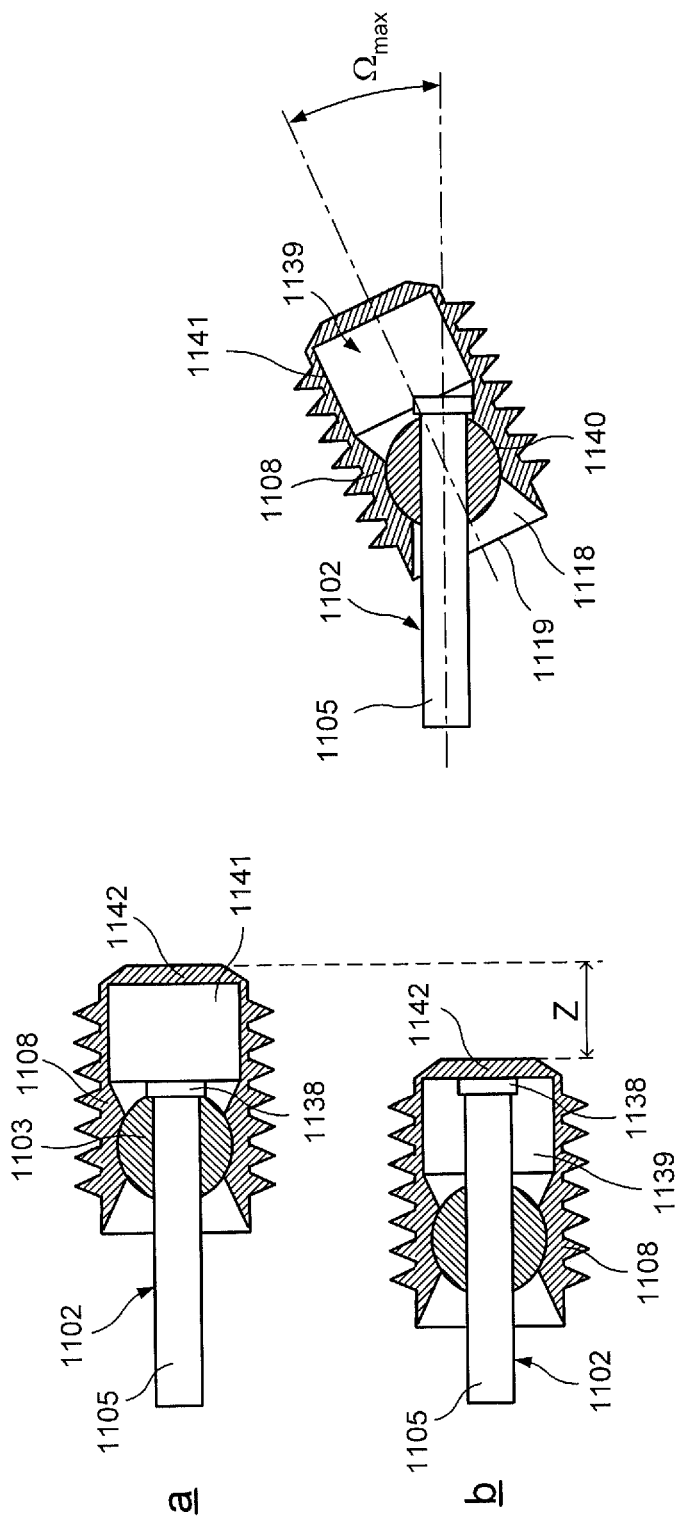
FIG. 26 illustrates the maximal angulation without axial dynamization in a longitudinal section through a front portion of a fixation element according to FIG. 23.

Once the fixation element 1102 has been advanced into the bone, the sleeve 1137 is slid distally over said the proximal portion 1145 of the shaft 1105 of the fixation element 1102 and inserted into the portion of the bore 1110 which extends within the shaft fragment of the humerus. The shaft 1105 of the fixation element 1102 is axially guided within the central bore 1143 of the sleeve 1137. The transverse hole 1146a of the longitudinal shaft 1105 and the transverse hole 1146b of the sleeve 1137 are aligned to receive the bone screw 1124 to fix the sleeve 1137 and the fixation element 1102 in the bone. The spherical head segment 1103 and the anchoring element 1108 attached thereto are slidably arranged on the shaft 1105 of the fixation element 1102. The slidable arrangement between the shaft 1105 of the fixation element 2 and the anchoring element 1108 allows the anchoring element 1108 to move axially thus allowing a dynamization of the fracture in the direction of the central axis 1117 of the fixation element 1102 as illustrated in FIG. 24. A maximum axial displacement Z of the anchoring element 1108 relative to the shaft 1105 of the fixation element 1102 is limited by the head 1138 of the fixation element 1102 which abuts against the spherical head element 1103 when the anchoring element 1108 is in its fully advanced position, as shown in FIG. 25a, and which abuts the distal end 1142 of the cavity 1139 when the anchoring element 1108 is in its retracted position, as shown in FIG. 25b. The angulation between the anchoring element 1108 and the shaft 1105 of the fixation element 1102, as shown in FIG. 26, is limited by either the opening 1118 at the proximal end 1134 of the anchoring element 1108 or by the cylindrical section 1141 of the cavity 1139 which accommodates the head 1138 at the first end 1147 of the shaft 1105. Thus, the anchoring element 1108 and the shaft 1105 of the fixation element 1102 has a maximum angle of angulation $\Omega_{max}$ when the anchoring element 1108 is in its fully extended position as illustrated in FIG. 26.

FIGS. 27 to 30 illustrate another exemplary embodiment of a bone implant 1200, which is substantially similar to the bone implant 1, as described above, comprising a fixation element 1202 which may be inserted through an opening of a bone plate 1206 into a femoral head bone fragment. The bone implant 1200, however, differs from the bone plate 1 only therein that the bone plate 1206 comprises a pivotable sleeve 1252 rather than a barrel fixed thereto. The sleeve 1252 extends through a bore 1251 in the bone plate 1206 and may be affixed to the bone plate 1206 via two radially extending connecting elements 1249, which permit the sleeve 1252 to pivot thereabout. The bore 1251 has a larger diameter than an outer diameter of the sleeve 1252 such that the sleeve 1252 may be pivoted within the bore 1251. In a cross-section orthogonal to a central axis 1217 of the shaft 1205, the two connecting elements 1249 are located on diametrically opposed sides of the sleeve 1252 and may be integrally formed with or coupled to the inner wall 1254 of the bore 1251. The connecting elements 1249 of the sleeve 1252 may be received within corresponding recesses in the inner wall 1254 of the bore 1251 such that the sleeve 1252 is pivotably coupled to the bore 1251. Alternatively, the connecting elements 1249 may be integrally formed with or fixed to the sleeve 1252 such that the connecting elements 1249 may be plastically deformed to define a pivot axis 1253 extending orthogonal to the central axis 1217 of the shaft 1205. Thus, the connecting elements 1249 form a joint 1250 including two coaxially arranged and plastically deformable pivot pins between the sleeve 1252 and the bore hole 1251 of the bone plate 6. Alternatively, the joint 1250 may be configured as a cardan joint including two pairs of pivot pins orthogonally arranged with respect to each other.

Various embodiments of an osteosynthetic implant including an embedded hinge or cardan joint are described in U.S. Pat. No. 6,663,632 to FRIGG. The entire content of the aforementioned document is incorporated herein by reference thereto.

Figure 29:
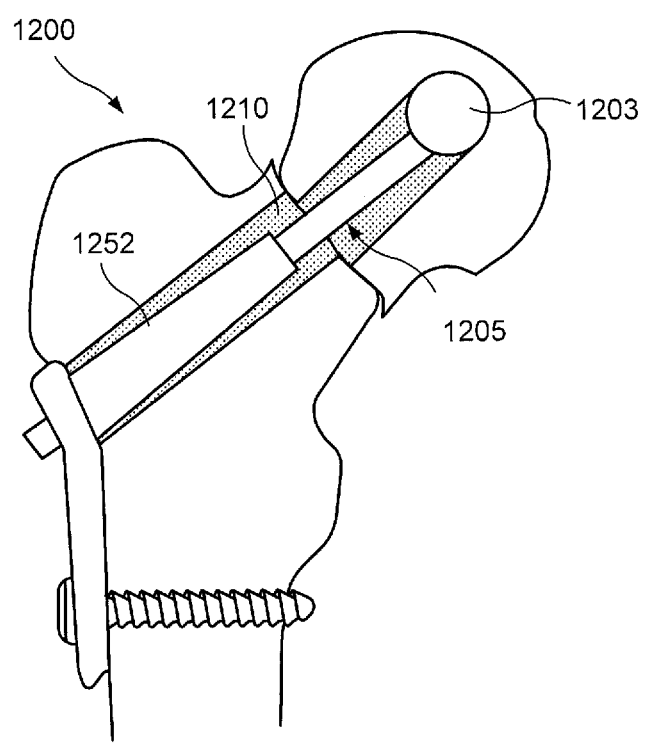
FIG. 29 illustrates a lateral view of the embodiment of the bone implant of FIG. 27 with the femoral head fragment rotated about the spherical head element.
Figure 31:
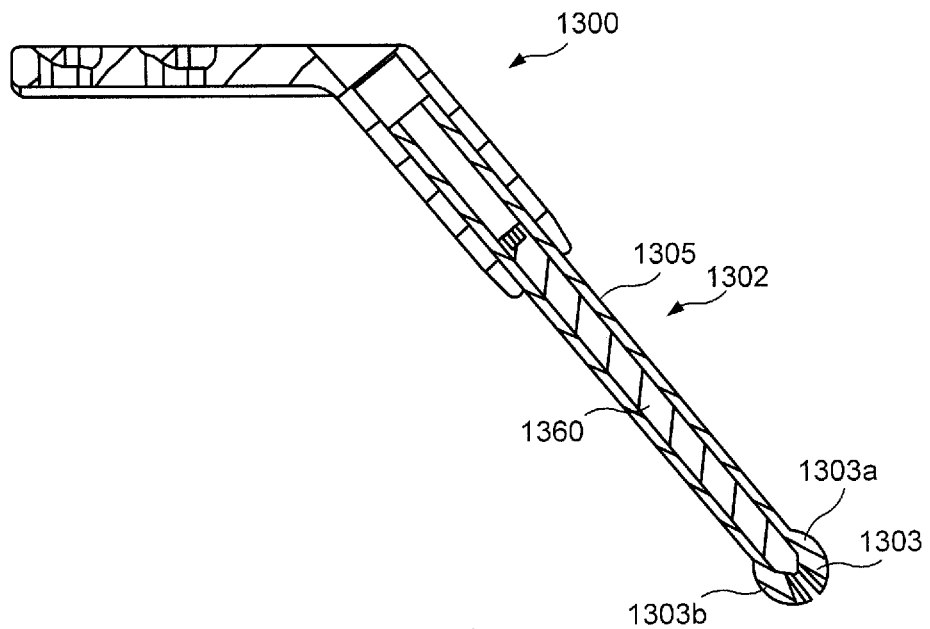
FIG. 31 illustrates a sectional view of yet another embodiment of the bone implant according to the invention in a first non-expanded configuration.
Figure 32:
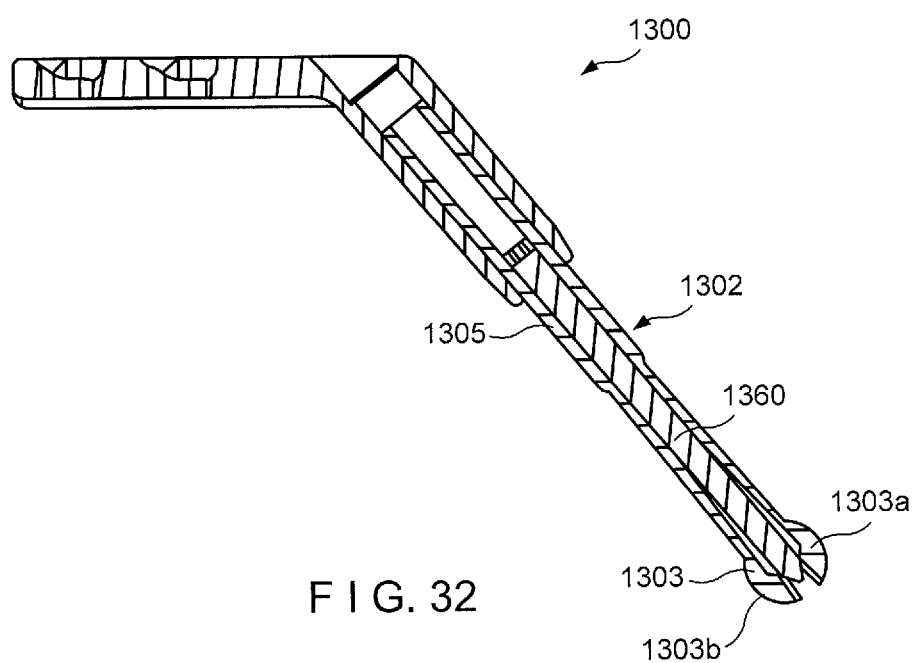
FIG. 32 illustrates a section view of the embodiment shown in FIG. 31 in a second expanded configuration.

As illustrated in FIG. 27, the fixation element 1202 is inserted through a bore hole 1210 drilled into the bone such that the spherical head element 1203 is seated within the femoral head bone fragment. The sleeve 1252 is mounted on a proximal portion of the shaft 1205 so that the femoral head fragment may pivot about the spherical head element 1203, as illustrated in FIG. 29. The bone implant 1200 then permits the femoral head to be displaced in a direction A, as shown in FIG. 30, by pivoting the sleeve 1252 about a pivot axis 1253 defined by the connecting elements 1249 as indicated by arrow B in FIG. 30. The sleeve 1252 is pivoted about the pivot axis 1253 via, for example, a relatively long lever instrument which exerts a large force onto the plastically deformable connecting elements 1249. The force exerted onto the connecting elements 1249 via the lever is much higher than any force which can occur anatomically on the femoral head so that once the deformation of the connecting elements 1249 has taken place, the connecting elements 1249 remain stable (e.g., deformed) providing sufficient stability to the bone implant 1200. It will be understood by those of skill in the art that the above-described articulated connection between the shaft 1205 of the fixation element 1202 and the bone plate 1206 via the sleeve 1252 may be similarly applied to a bone implant including an intramedullary nail, as shown in FIG. 7, rather than a bone plate. Where bone implant 1200 comprises an intramedullary nail, the sleeve 1252 may be configured as a bushing insertable through a through bore and coupleable thereto via a connection similar to the above described joint 1250. Similarly, the above-described articulated connection may also be applied to the bone implant 1100, as shown in FIGS. 23 and 24.

Another exemplary embodiment of the present invention is shown in FIGS. 31 to 34. This embodiment of a bone implant 1300 is substantially similar to embodiments shown in FIGS. 1, 2, 27, 28 and 29. In this exemplary embodiment the bone implant 1300 comprises a fixation element 1302 including a spherical head element 1303 that is expandable to increase the radius from a first radius to a second radius for anchoring the fixation element in the bone fragment. The spherical head element 1303 has a slit arranged to divide it into expandable parts 1303a, 1303b. The expandable parts 1303a, 1303b are connected at proximal ends 1350a, 1350b to a shaft 1305. The opposed distal ends 1351a, 1351b of the expandable parts 1303a, 1303b are unconnected and are expandable relative to the connection point at the proximal end 1350a, 1350b. As would be understood by the skilled person, the expandable parts 1303a, 1303b can have a uniform separation across the slit, they can taper from the proximal end to the distal end, or they can have any other suitable starting, reduced diameter, configuration. A cannulation 1321 within the shaft 1305 that allows, for example, a K-wire to be received by the fixation element 1302 for guidance purposes can extend into the spherical head element 1303. To expand the expandable parts 1303a, 1303b, a tool 1360 with a tapered engagement end (not shown) is pushed down the cannulation and into engagement with the expandable parts 1303a, 1303b. The spherical head element 1303 shows two expandable parts 1303a, 1303b. However, as would be understood by the skilled person, the spherical head element can be divided into any number of expandable parts to allow the head element 1303 to be expanded.

In the embodiment where the expandable parts have uniform separation across the slit, the diameter of the cannulation 1321 is greater than the separation. The tool 1360, having a greater diameter than the separation, is inserted into the spherical head element 1303 to expand the head element 1303. The expansion from the reduced diameter configuration to the increased diameter configuration is achieved by pushing the tool 1360 in between the expandable parts 1303a, 1303b to force them apart due to the greater diameter of the tool 1360.

In the embodiment where the expandable parts 1303a, 1303b taper towards each other, the cannulation 1321 can have the same diameter or an increased diameter depending on the amount of expansion required. As would be understood by the skilled person, the expansion is achieved due to the tool acting on the wall to straighten or expand the taper.

Although the invention and its advantages have been described in detail, it should be understood that various changes, substitutions, and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, composition of matter, means, methods, or steps, presently existing or later to be developed that perform substantially the same function or achieve substantially the same result as the corresponding embodiments described herein may be utilized according to the present invention. It will be appreciated by those skilled in the art that various modifications and alterations of the invention can be made without departing from the broad scope of the appended claims. Some of these have been discussed above and others will be apparent to those skilled in the art.

What is claimed is:

1. A fixation device for treating an epiphyseal fracture of a long bone, comprising:
   a shaft extending longitudinally along a central axis from a first end to a second end configured to slidably engage an opening of a bone implant, the central axis of the shaft being coaxial with a central axis of the device;
   a bone anchoring element pivotally coupled to the first end of the shaft, the bone anchoring element including a spherical cavity, wherein the central axis of the shaft extends through a center of the spherical cavity, the spherical cavity mechanically retaining a ball at the first end of the shaft therein to form a ball and socket joint so that, the bone anchoring element is pivotable relative to the central axis of the shaft, the bone anchoring element further including a threading extending about an outer surface thereof for engaging a fragment portion of bone when inserted therein, wherein the shaft is sized such that, during use, the shaft extends through a neck of the bone and the ball extends at least partially into a head of the long bone.

2. The device according to claim 1, wherein the bone anchoring element is longitudinally movable relative to the central axis of the shaft.

3. The device according to claim 1, wherein the bone anchoring element is not coaxial with the central axis of the shaft.

4. The device according to claim 1, wherein the spherical cavity includes a tapered proximal end.

5. The device according to claim 1, wherein a diameter of the bone anchoring element is larger than a diameter of the shaft.

6. A system for treating an epiphyseal fracture of a long bone, comprising:
   an elongated bone implant extending along a longitudinal axis and including an opening extending therethrough; and
   a bone fixation device, including:
      a shaft extending along a central axis from a distal end to a proximal end configured to slidably engage the opening of the bone implant, the central axis of the shaft being coaxial with a central axis of the bone fixation device; and
      a bone anchoring element pivotally coupled to the distal end of the shaft by a ball and socket joint and having a diameter that is larger than a diameter of the shaft, wherein the central axis of the shaft extends through a center of the ball and socket joint, the bone anchoring element including a threading extending around an outer surface thereof for engaging bone which it is inserted wherein the shaft is sized such that, during use, the shaft extends through a neck of the long bone and the ball extends at least partially into a head of the long bone.

7. A method for treating an epiphyseal fracture of the long bone comprising the following steps:
   positioning a guide wire in a long bone in a direction transverse to a longitudinal axis of the long bone and penetrating through a shaft fragment of the long bone and into an epiphyseal fragment;
   drilling a bore hole into the long bone from a lateral surface thereof; and
   threading a fixation device into the bore hole so that a bone anchoring element pivotally coupled to a distal end of a shaft via a ball and socket joint is positioned within a desired portion of a fragmented bone portion such that the fragmented bone portion is pivotable relative to a central axis of the shaft when the fixation device is in an inserted position, wherein in the inserted position, the shaft extends through a neck of the long bone and the ball and socket joint extends at least partially into a head of the long bone, the central axis of the shaft being coaxial with a central axis of the fixation device, and wherein the central axis of the shaft extends through a center of the ball and socket joint.

8. The method according to claim 7, further comprising positioning a bone implant along a length of the long bone such that a proximal portion of the longitudinal shaft slidably engages an opening thereof.

9. The method according to claim 8, wherein positioning the bone implant includes inserting an intramedullary nail into the medullary cavity of the long bone.

10. The method according to claim 8, wherein positioning the bone implant includes arranging a bone plate along a portion of a length of the bone.

* * * * *